(12) United States Patent
Doyle

(10) Patent No.: US 6,458,126 B1
(45) Date of Patent: Oct. 1, 2002

(54) ELECTROSURGICAL SUCTION AND COAGULATION INSTRUMENT

(76) Inventor: Donald E. Doyle, 4105 Hospital Rd., Suite 102-A, Pascoagoula, MS (US) 39581

(*) Notice: Subject to any disclaimer, the term of this patent is extended or adjusted under 35 U.S.C. 154(b) by 0 days.

(21) Appl. No.: 09/551,440

(22) Filed: Apr. 18, 2000

Related U.S. Application Data

(63) Continuation-in-part of application No. 09/156,454, filed on Sep. 19, 1998, now abandoned.

(51) Int. Cl.7 .............................................. A61B 18/18
(52) U.S. Cl. .................................... 606/49; 606/41
(58) Field of Search ................... 606/41, 42, 45–50; 604/21, 22

(56) References Cited

U.S. PATENT DOCUMENTS

| | | | |
|---|---|---|---|
| 3,974,833 A | * 8/1976 | Durden, III | 606/48 |
| 5,267,994 A | * 12/1993 | Gentelia et al. | 606/15 |
| 5,290,282 A | * 3/1994 | Casscells | 606/29 |
| 5,324,254 A | * 6/1994 | Philips | 604/21 |
| 5,395,312 A | * 3/1995 | Desai | 604/22 |
| 5,401,274 A | * 3/1995 | Kusunoki | 606/41 |
| 5,830,214 A | * 11/1998 | Flom et al. | 606/41 |

* cited by examiner

*Primary Examiner*—Michael Peffley
(74) *Attorney, Agent, or Firm*—Roger A. Marrs

(57) ABSTRACT

A combined device for simultaneously dissecting tissue, suctioning loose tissue and coagulating tissue during a surgical procedure having a hand-held elongated housing supporting an elongated body enclosing a metallic suction tube electrically conductive wherein the tube terminates at the distal end with an opening adjacent to an integrally formed electrical element. The tube is covered with insulation with the element exposed to provide a tissue dissecting and coagulating surface. Therefore, the electrical element serves to sever tissue as well as to coagulate simultaneously with suctioning of fluids from the surgical area.

3 Claims, 1 Drawing Sheet

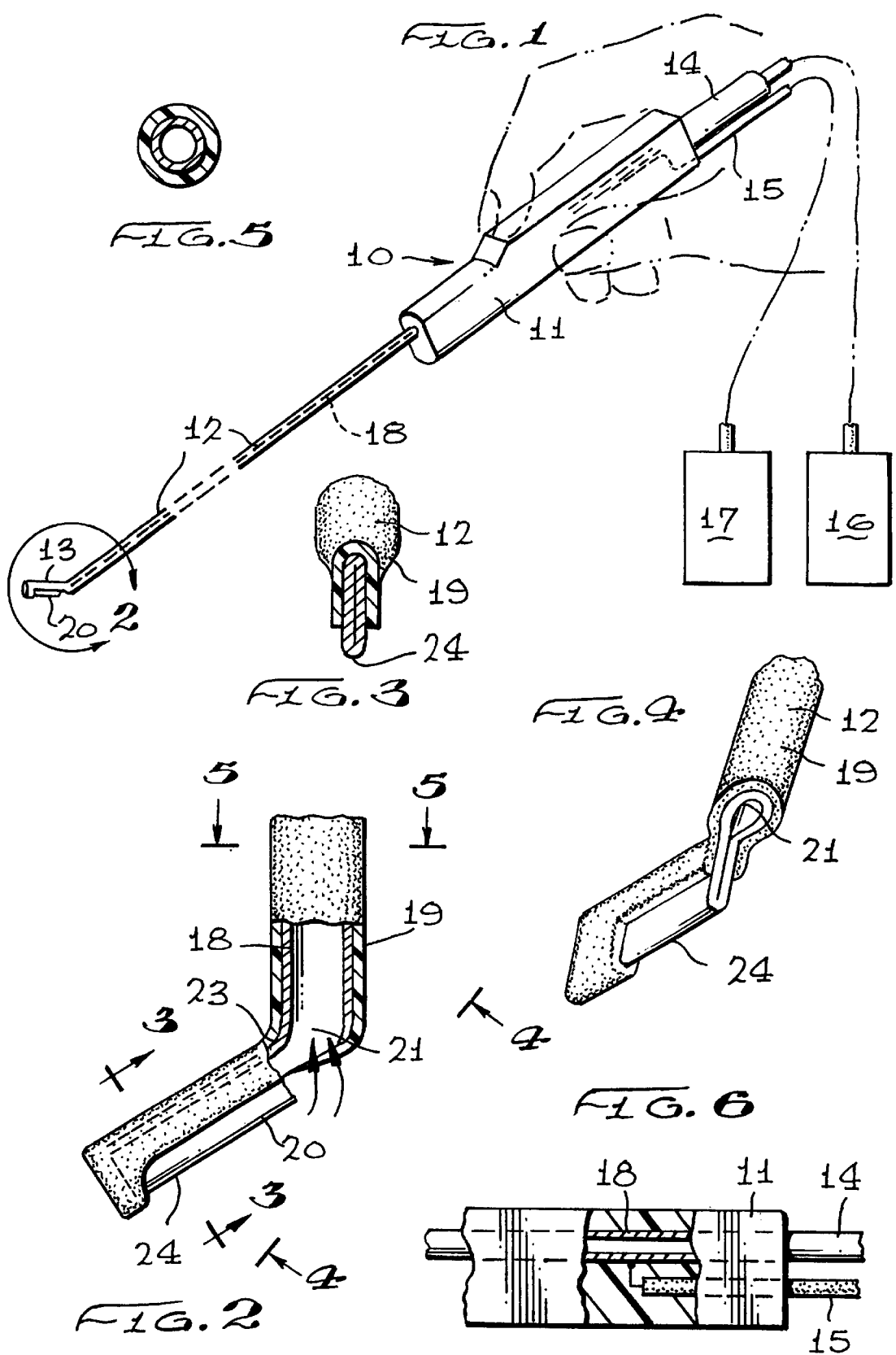

US 6,458,126 B1

ELECTROSURGICAL SUCTION AND COAGULATION INSTRUMENT

This application is a continuation in part of U.S. Ser. No. 09/156,454 filed Sep. 19, 1998 (now abandoned).

BACKGROUND OF THE INVENTION

1. Field of the Invention

The present invention relates to the field of medical instruments, and more particularly to a combined electro-coagulator-suction instrument having simultaneous dissecting, coagulating and suctioning capabilities.

2. Brief Description of the prior Art

In the past, it has been the conventional practice to use an electro-coagulator and suction instrument for coagulating bleeding capillaries within a surgical field and for drawing out blood and other liquids from the field either during, before, or after the coagulation procedure. Such conventional devices are especially useful for Epistaxis procedures. Typical examples of such devices are disclosed in U.S. Pat. Nos. 5,810,806; 5,833,689 and 5,324,254.

Although useful for their intended purpose, the prior art suction coagulators do not have a means for cutting, severing or dissecting tissue simultaneously with the coagulation and suction procedures. The conventional suction coagulator instrument terminates in a rounded or tapered tip that is electrified so as to perform the coagulation requirement and generally the tip extends outwardly from a suction tube which is coaxially disposed with respect to the tip. In such a location, the covering or casing for the suction device and the electro-coagulating device are not conducive for severing or dissecting tissue.

Therefore, a long-standing need has existed in the surgical field to provide a combined suction, coagulator and dissecting device or instrument which will simultaneously perform the procedures of severing tissue, drawing out blood and other liquids and coagulating bleeding capillaries.

SUMMARY OF THE INVENTION

Accordingly, the above problems and difficulties are avoided by the present invention which provides a novel combined cutting, suctioning, and coagulating instrument for simultaneously performing these procedures during surgical operations. The instrument includes an elongated housing having an outwardly projecting extension that terminates at its distal end with a combined thermo electro cutting or dissecting element immediately adjacent to an opening leading into a suction tube. The combined element is formed by compressing the tube wall into a flat cutter and drilling or otherwise removing a small section of tube wall material at one end of the cutter to provide an entrance or opening leading into the passageway of the suction tube. The suction tube is covered with electrical insulative material with a portion of the material removed to expose a portion of the combined element. An electrical power supply is connected to the conductive suction tube to energize the combined cutter element while a suction pump is coupled to the suction tube to provide a suction force for drawing fluids, tissue, debris or the like from surrounding tissue during the operating procedure. The insulation around the suction tube prevents inadvertent touching of the electrified tube material from inadvertently damaging or injuring nearby tissue. Only the exposed portion of the combined cutter element extends through and beyond the insulated material. The combined cutter element juts laterally away from the central longitudinal axis of the major length of the suction tube at an approximate angle of forty-five degrees.

Therefore, the electrical element serves to sever tissue as well as to coagulate simultaneously with suctioning of fluids from the surgical area.

Accordingly, it is among the primary objects of the present invention to provide a combined electro-coagulator-suction-dissecting instrument which is useful for simultaneously coagulating bleeding capillaries while severing tissue and suctioning fluids within a surgical field.

Another object of the present invention is to provide a novel electro-coagulator which will simultaneously suction and dissect tissue in a convenient and comfortable manner for both the surgeon and the patient.

Still another object of the present invention is to provide a novel surgical device which simultaneously severs tissue, coagulates and draws fluid by way of suction wherein the instrument performs these procedures at the distal end of an elongated extension or body and wherein the coagulator and severing electrical element is immediately ahead of and angularly disposed with respect to the longitudinal axis of a suction tube.

Another object is to provide the distal end of a surgical device which is quasi or semi-malleable, formed by compressing the wall of a suction tube and which will permit simultaneous suction, coagulation and dissecting medical procedures.

Still a further object of the present invention is to provide a novel surgical instrument which includes a distal terminating end having an exposed electrical element and suction means for simultaneous suction, coagulation and dissection which will lower blood loss and shorten surgical time.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a diagrammatic perspective view showing the novel medical instrument incorporating the present invention;

FIG. 2 is an enlarged perspective fragmentary view illustrating the distal or terminating end of the instrument illustrated in FIG. 1 and which serves as a thermo-electric cutting element immediately adjacent to an entrance to a suction tube;

FIG. 3 is a transverse cross-sectional view of the distal end taken in the direction of arrows 3—3 of FIG. 2;

FIG. 4 is a perspective view of the suction tube opening and the combined cutter and coagulator element as taken in the direction of arrows 4—4 of FIG. 2;

FIG. 5 is a transverse cross-sectional view of the insulated electrically conductive suction tube shown in FIG. 2 in the direction of arrows 5—5 thereof; and FIG. 6 is an enlarged fragmentary view in section illustrating the electrical connection of the conductive suction tube with a power supply.

DESCRIPTION OF PREFERRED EMBODIMENT

Referring to FIG. 1, the novel medical instrument of the present invention is illustrated in the general direction of arrow 10 which includes an elongated housing 11 having a forward end which supports an elongated extension or body 12 terminating at its distal end in a tip 13. The opposite end of housing 11 from its end supporting the extension 12 includes mounting of a suction hose 14 and an electrical wire 15. The suction hose 14 terminates at its opposite end with a suction pump 16 while the electrical wire terminates in a power supply 17.

The extension 12 is rigid and includes an electrically conductive metallic suction tube 18 covered with an insulated material 19. The tip 13 is angularly disposed with respect to the central longitudinal axis of extension 12 at approximately forty-five degrees. A portion of the insulative material is removed from the suction tube 18 at the tip 13 to expose a combined cutter and coagulator element 20. The element is formed by bending the suction tube to the desired angle followed by pressing or compressing the conductive wall of the tube together and removing the portion of insulation. The pressed tube wall results in the elongated element 20 having an exposed exterior surface of substantial length and width so as to provide a large surface or area for cutting tissue and coagulating the cut or severed tissue.

The exposed electrical cutter or element is indicated by numeral 20 in FIG. 2 while the suction tube opening is indicated by numeral 21. It is to be particularly noted that preferably, the tip 13 is arranged at a forty-five degree angle with respect to the major length of the extension positioned to suit the surgeon in order to better perform dissecting tissue procedures.

Referring now in detail to FIGS. 2 and 3, it can be seen that the tube end at tip 13 is bent at location 23 with the element 20 formed by pressing the tube wall into a flat sided structure. The element is rounded at numeral 24. The electrical element 20 is integrally joined with the tube 18. The suction tube includes insulation covering the tube 18 and the insulation has been removed at the tip 13 in order to expose the element 20 which then constitutes a tissue cutting element as well as a coagulating element. It is to be particularly noted that the exposed element 20 is even with or ahead of an opening 21 in the suction tube through which severed tissue, fluids or the like are drawn. Only a portion of the insulation on tube 18 has been removed to expose the elongated and flat-sided electrical element 20.

With respect to FIG. 3, it can be seen that a portion of the insulation on the tube 18 remains so that a portion of the electrical element is exposed. The electrical element 20 and the opening in the suction tube 18 are in close proximity so that simultaneous dissection of tissue and coagulation thereof occurs simultaneously with suction of any liquids or fluids.

FIG. 4 illustrates the opening 21 and the integral joining of the element 20 at the location 23 with the tube.

FIG. 5 is a cross section of the tube and the covering insulation since the metallic tube is electrified to heat the element 20.

FIG. 6 shows an electrical connection of the power supply wire 15 with the metallic suction tube. The housing is composed of insulative material.

In view of the foregoing, it can be seen that the device of the present invention facilitates and expedites surgical operation, such as tonsillectomies or the like. In practice, a tonsillectomy is a procedure which can produce copious bleeding which is not only hazardous to the patient but causes a longer surgical and anaesthetic time. Currently available suction-coagulator devices aid in decreasing blood loss but incorporate a rounded tip for the electrical element and as such, do not provide an operative area as an efficient tissue dissecting tool or operative face. The inventive combined suction, coagulator and dissecting device of the present invention not only lowers blood loss but shortens surgical time as well. Also, by the use of the inventive instrument, the tip 13 can be positioned or shaped to a desired configuration.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. An electrosurgical instrument comprising:
   a housing;
   an elongated metallic suction tube having a major longitudinal axis;
   said suction tube having a first back portion fixly mounted in said housing and a second front portion outwardly projecting from said housing;
   an electric insulative material covering carried on said suction tube;
   said suction tube terminating at its distal end with an integral metallic element free of said insulative material and having an external surface area exposed beyond said insulative material;
   said metallic element adapted to simultaneously dissect and cauterize tissue;
   said suction tube having an opening immediately adjacent said metallic element for withdrawing dissected tissue simultaneously from a surgical area;
   said distal end of said suction tube is disposed at a forty-five degree angle with respect to said major axis; and
   said metallic element is joined with said suction tube by a bent portion of said suction tube.

2. The electrosurgical instrument as defined in claim 1 wherein:
   said metallic element is integral with said suction tube wherein said suction tube at its distal end is compressed together.

3. The electrosurgical instrument as defined in claim 2 including:
   a power source connected to said metallic suction tube; and
   a suction pump operably coupled to said suction tube.

* * * * *